United States Patent
Mitogo

(10) Patent No.: US 11,147,511 B1
(45) Date of Patent: Oct. 19, 2021

(54) REX WEAR: "BRACELET"

(71) Applicant: Donaldo Rex Mitogo, Providence, RI (US)

(72) Inventor: Donaldo Rex Mitogo, Providence, RI (US)

( * ) Notice: Subject to any disclaimer, the term of this patent is extended or adjusted under 35 U.S.C. 154(b) by 0 days.

(21) Appl. No.: 16/873,826

(22) Filed: Jul. 20, 2020

(51) Int. Cl.
*G08B 21/00* (2006.01)
*A61B 5/00* (2006.01)
*G08B 5/36* (2006.01)
*G08B 21/02* (2006.01)

(52) U.S. Cl.
CPC .......... *A61B 5/6824* (2013.01); *A61B 5/4845* (2013.01); *A61B 5/746* (2013.01); *A61B 5/7445* (2013.01); *G08B 5/36* (2013.01); *G08B 21/02* (2013.01)

(58) Field of Classification Search
CPC ... A61B 5/6824; A61B 5/7445; A61B 5/4845; A61B 5/746; G08B 5/36; G08B 21/02
USPC ......................................................... 340/576
See application file for complete search history.

(56) References Cited

U.S. PATENT DOCUMENTS

| | | | |
|---|---|---|---|
| 2017/0065224 A1* | 3/2017 | Rahko | A61B 5/6824 |
| 2019/0206538 A1* | 7/2019 | Xing | G06Q 20/3829 |
| 2019/0290197 A1* | 9/2019 | Nothacker | A61B 10/0064 |
| 2019/0388016 A1* | 12/2019 | Lewis | A61B 5/6831 |
| 2020/0145717 A1* | 5/2020 | Shah | H04N 21/43615 |

* cited by examiner

*Primary Examiner* — Mark S Rushing

(57) ABSTRACT

The bracelet features a full screen hand-wear with multiple sensors. The bracelet is packed with advanced sensors to scan the user's finger prints in order to operate. The sensors are also used to check body mass index, heart rate, blood pressure, calories levels, body temperature, and more. The bracelet has digital keys installment, allowing the user to safely and securely install the digital codes of their vehicle's remote controller or house's digital lock. In this way, the bracelet can lock and unlock the vehicle, house, or any other utility hardware or device that uses digital key for operations. With the sole purpose of converting humanitarian tasks relatively easy and efficient. You can carry all of your keys in one bracelet, in addition to, phone calls, messages, internet, social media, cameras, & your body's alcohol consumption level tracker.

2 Claims, 1 Drawing Sheet

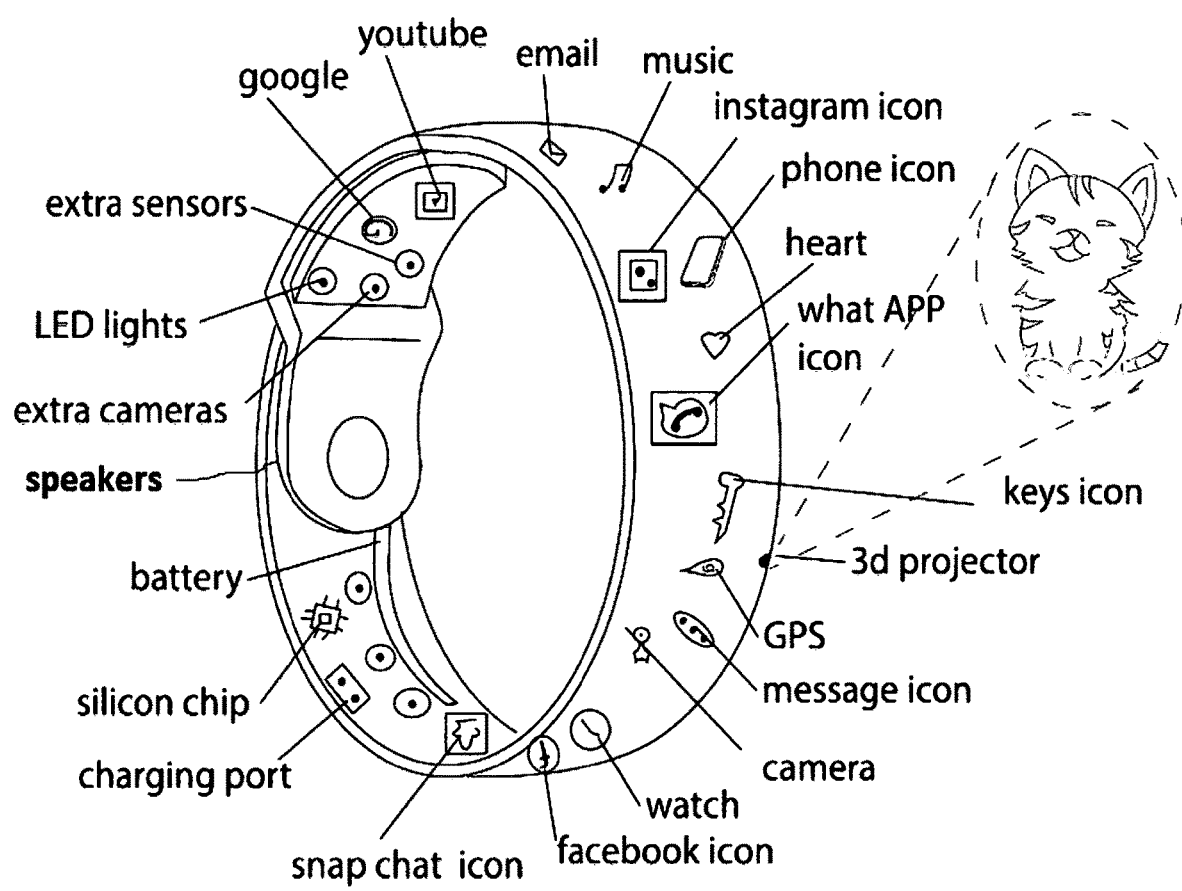

REX WEAR: "BRACELET"

FIELD OF INVENTION

The bracelet is a cutting-edged technological device designed to save lives by using its sensors to measure the user's alcohol consumption levels and stopping the possibilities of drunk driving. The bracelet is packed with eccentric sensors, uniquely designed to measure the level of alcohol consumed by a person. Instead of traditional drunk driving reports or spotted then pulled over by the police scenarios. The Mitogo intoxicate bracelet automatically does the work and saves a lot of time, hostile, and other dangerous possibilities. The purpose of this device is to save the lives of million drunk drivers and to eliminate the daily hassles such as forgetting car/house keys, cell phone, and much more. The bracelet is a one stop for all purpose device, it features a full-glass hand wear wrist band with an additional 3D hologram projector for a bigger visual expansion. The bracelet is a nonobvious device uniquely crafted to serve many different purposes but to all which are part of basic life necessities. The device comes equipped with supreme micro-sensors embedded with ultra-sensitive mini cameras: the sensors detect the user's finger prints for privacy and security login. The mini cameras are in used for "360×" view and photo or video captures. The eccentric sensors also provide the unique "Rex DNA Coloring" the Red, Green, & Blue colors for alcohol consumption tracking. The entire bracelet glows in color "Green" when the user has a low alcohol in their system, it glows "Blue" when the level of alcohol consumption is high, and it glows "Red" when the alcohol consumption is too high in the user's system. Allowing the bracelet to disable driving accessibility and communicate the emergency contacts according to the bracelet's programming set up. The bracelet comes with all around build-in LED lights, to illuminate different colors depending on the programming commands and functions. A sophisticated Global positioning system (GPS), to assist the user to navigate from unknown locations. Wi-Fi & Bluetooth connectivity capabilities. 1 TB memory, and a built-in battery to ensure the long-lasting usage capability for up forty-eight (48) hours battery. Inside of the device, you will find the advanced Silicon Chip: one of the world's most available substances, excitedly abundant in all parts of the world and extraordinarily efficient. Silicon Chips are capable of executing thousands if not millions of commands at the same time. And this Silicon chip is the heart of the device. The bracelet is operated by a silicon chip which gives the invention an environment friendly and extremely cheap to make.

BRIEF SUMMARY OF THE INVENTION

How does it Work

For the criticality of this innovation, it is imperative that the bracelet performs the following functions. When the digital keys are installed into the user's bracelet, the bracelet will perform the following operations: if the user of the bracelet is drinking, the bracelet will use its eccentric sensors to measure the alcohol level in the person's body. If the level is small: the entire bracelets will glow in color Green. If the levels are somewhat high: the bracelet will glow in the color Blue, and when the person is extremely drunk: the bracelet will glow in the color Red. Also, depending on the type of vehicle the user is driving the bracelet will behave accordingly, if it's a late model vehicle with a traditional metal key, the bracelet will not allow the driver to enter the vehicle. It will send alert messages to the emergency contacts saved on the bracelet's software indicating that the bracelet's user is too drunk to drive. If it's a newer vehicle with the "push start button", the bracelet will allow the driver to enter the vehicle, but will not allow the driver to start the ignition, but rather, will continue with sending alert system protocol. The finger prints are designed as a secure log-in feature, to ensure the maximum-security level and data protection measurements. The bracelet also supports all cellular communications, including 5G cellular capability, fast messaging system, Advanced GPS, 4K cameras, eccentric sensors, and much more. The ideology of this device stems from the advancement of modern technology and the commitment of always innovating beyond our limits. This bracelet is designed to be the most sophisticated and the single most advanced technological bracelet ever created. The bracelet has its unique functions and performs critically in the most desirable ways in accord to its programmable software features.

BENEFIT SUMMARY

To reduce the amount of radio waves and other stressful situations that strangles our lives little by little. The Mitogo intoxicated bracelet is designed to be the simplest bracelet that one can wear and execute and respond to all of the digital obligations. Instead of multiple devices (work and personal cell phone, work tablet, computer, or a USB drive), all of these things could be intergraded into one simple bracelet and it all can be done with one simple and luxurious bracelet's operating system. The bracelet can take two SIM cards for cellular network, advanced and fast messaging system, supporting all social media applications and websites, advanced search engines, more space to work with including an additional 3D hologram for presentations and more. Furthermore, the bracelet can be connected to any smartphone, while boosting the innovation and ensuring the meaning of advanced technology. The Mitogo intoxicate bracelet can also be used as an office or home hotspot wireless network.

DESCRIPTION OF RELATED ART

There exist regular smart watches such as: "Apple Watch, Samsung Watch, Fitbit, and other types of smart watches, but never have there been in existence a sophisticated advanced technological bracelet with alien digital capabilities such as that of the Mitogo intoxicated bracelet. Unlike traditional smart watches, this bracelet is far more advanced and excessively easy to use. The bracelet is also cheap to manufacture as it comes with silicon chips and gorilla glass all around the bracelet. The bracelet is superiorly design to surpass any modern smart watch currently in the market. Although the bracelet is made cheap to manufacture, environmentally friendly due to its components, but its digital capabilities are far beyond modern technology. With its 1,000 GB memory, long lasting battery, silicon chips, advanced eccentric sensors, 4K cameras, surround sound speakers, 5G cellular network capability, Hotspot wireless network, 3D hologram projector, natural feel screen touch system, and the Rex DNA lighting. The Mitogo intoxicated bracelet is exceedingly supreme and unique.

DRAWING DESCRIPTION

Brief Description of the Drawings

As described above, the components of this device are comprised of silicon chip, battery, 4K cameras, surround sound speaker, 3D hologram projector, eccentric sensors, 1 TB memory, Wireless hotspot, 5G cellular network capability, full screen gorilla glass bracelet, and Rex coloring DNA functions. FIG. 1, showcases the technology, operation control of the device, and all of its components. FIG. 1, shows the inside technology of the bracelet; including specific parts and downloaded social media applications. The bracelet also shows a 3-Dimensional hologram image, plus, cell-phone, message, changing port, keys icon, GPS, and much more extended applications and the bracelet's supreme digital capabilities.

The presented advanced digital bracelet is the hybrid of home technology combined with portable technology, in order to bring about the best live supporting device that will allow humanity to fully perform full-time in the digital world as well as being full-time in personal and family obligations. Unlike cellphones, tablets, or computers that we often have to carry in our hands in order to be responsive in the digital world, the Mitogo Intoxicated Bracelet is almost invisible to our personal and family lives obligations. It is a simple and yet the most advanced bracelet that is more powerful than any cellphone or computer combined. The bracelet features a hand-crafted masterpiece wear with light-weight signature. Furthermore, unlike tradition smart watches where the user has to wear while holding the phone nearby, the Mitogo intoxicated Bracelet is fully independent, meaning you can leave your phone at home and go about your day with the same or even better performance digital device that will keep the user update and responsive digitally all day. The bracelet shown in FIG. 1, will come with satellite synchrony technology; meaning it will naturally be connected to your phone via satellite.

The invention claimed is:

1. An apparatus comprising:
a hand or wrist wear device featuring a full screen glass display, a silicon chip, battery, 4K micro-cameras, surround sound speaker, a 3-Dimensional hologram projector, sensors, LED, storage memory, a wireless hotspot, 5G cellular network capability, and Rex coloring DNA functions;
the apparatus featuring a glass screen that covers the entire hand or wrist wear device, a silicon chip that runs an operating system and a command central unit of the hand or wrist wear device;
the apparatus having a battery to power the device, including all around mini-cameras that allow the user to take 360 degree view photos or videos;
a surround sound speaker and a 3-Dimensional hologram projector: wherein the 3D imagery is created from the hand or wrist wear device and then, projecting via the 3-dimensional hologram technology; the sensors are programmed with commands to follow based on system software commands, and a device storage memory of 1,000 GB solid state drive, with the ability to install applications and store other data from user activity;
the apparatus uses a wireless hotspot and has 5G cellular network capability;
the hand or wrist wearable device has blue, green, and red LED lighting:
wherein the LED integrated into the device glow in "red", "green", and "blue" respectively and each color has a meaning, in regards to the apparatus;
the combination of sensors with the LED lighting form a role especially when the user is drinking, the LED lights glow "blue" when the user is just starting to drink and is not drunk yet, they glow in color "green" when the user is heavily drunk, but the user is still conscious, and they glow in the color "red" when the user is excessively intoxicated and has lost mental and physical control, and the user is unconscious;
depending on the type of vehicle the user is driving the hand or wrist wear device will behave accordingly, if the vehicle is a late model vehicle with a traditional metal key, the bracelet will deter the driver from entering the vehicle by sending alert messages to emergency contacts saved on the hand or wrist wear device's operating system.

2. The apparatus of claim 1 comprising:
the hand or wrist wear device containing the above described technology including touchless technology; including 6 feet distance sensors to distance the user from other people in surrounding areas; the 360 degree view multi-cameras used by the hand or wrist wear device to alarm the user to use a mask when the user is outdoors; a set of sensors equipped to monitor the user's heart-rate and blood pressure, some to which will help to avoid drunk-driving; and a form of dataset technology to remind the user to maintain extensive washing hands frequency throughout the day.

* * * * *